United States Patent
Mihalko et al.

(10) Patent No.: US 9,220,600 B2
(45) Date of Patent: Dec. 29, 2015

(54) KNEE PROSTHESIS

(75) Inventors: William Mihalko, Germantown, TN (US); Khaled J. Saleh, Springfield, IL (US); Said Moussa, Chamrandes (FR); Dominique Mouillet, Semoutiers (FR)

(73) Assignee: Aesculap Implant Systems, LLC, Center Valley, PA (US)

( * ) Notice: Subject to any disclaimer, the term of this patent is extended or adjusted under 35 U.S.C. 154(b) by 0 days.

(21) Appl. No.: 13/141,569

(22) PCT Filed: Dec. 22, 2009

(86) PCT No.: PCT/US2009/069163
§ 371 (c)(1),
(2), (4) Date: Dec. 14, 2011

(87) PCT Pub. No.: WO2010/075365
PCT Pub. Date: Jul. 1, 2010

(65) Prior Publication Data
US 2012/0095564 A1 Apr. 19, 2012

Related U.S. Application Data

(63) Continuation-in-part of application No. 12/484,594, filed on Jun. 15, 2009, now abandoned.

(60) Provisional application No. 61/140,183, filed on Dec. 23, 2008.

(51) Int. Cl.
*A61F 2/38* (2006.01)
*A61F 2/30* (2006.01)

(52) U.S. Cl.
CPC .................. *A61F 2/38* (2013.01); *A61F 2/3886* (2013.01); *A61F 2002/30116* (2013.01); *A61F 2002/30688* (2013.01); *A61F 2230/0006* (2013.01)

(58) Field of Classification Search
CPC .......................................... A61F 2/38
USPC ........................................... 623/20.21–20.28
See application file for complete search history.

(56) References Cited

U.S. PATENT DOCUMENTS

| 4,209,861 A | 7/1980 | Walker |
| 4,213,209 A | 7/1980 | Insall |

(Continued)

FOREIGN PATENT DOCUMENTS

| DE | 3101789 C2 | 1/1991 |
| DE | 69009509 T2 | 9/1994 |

(Continued)

OTHER PUBLICATIONS

Blaha, J. David, M.D., The Rationale for a Total Knee Implant That Confers Anteroposterior Stability Throughout Range of Motion, The Journal of Arthroplasty, vol., 19, No. 4, Suppl. 1 2004, Elsevier, Inc. 2004, USA.

(Continued)

*Primary Examiner* — Jason-Dennis Stewart
(74) *Attorney, Agent, or Firm* — RatnerPrestia

(57) ABSTRACT

A knee prosthesis having a femoral component with two condyles, an opening disposed between the two condyles, and a tibial component having bearing surfaces to engage and support each of the femoral component condyles. Moving the femoral and tibial components in flexion from about 0° to about 165° causes medial pivot rotation of the femoral component upon the tibial component. Rotation may be caused by interaction between an asymmetrical cam extending between the femoral condyles and a post disposed between the bearing surfaces and extending superior from the tibial component. Rotation may alternatively be caused by asymmetrical medial and lateral condyles which translate posteriorly upon respective medial and lateral bearing surfaces at disparate rates, without a femoral cam, a tibial post, or a post/cam contact surface. Embodiments of the knee prosthesis may be used in cruciate-substituting or cruciate-retaining procedures. Embodiments of the knee prosthesis may also prevent roll forward.

20 Claims, 15 Drawing Sheets

(56) References Cited

U.S. PATENT DOCUMENTS

| | | | |
|---|---|---|---|
| 4,298,992 | A | 11/1981 | Burstein |
| 5,007,933 | A | 4/1991 | Sidebotham |
| 5,147,405 | A | 9/1992 | Van zile |
| 5,219,362 | A * | 6/1993 | Tuke et al. ............... 623/20.31 |
| 5,236,461 | A | 8/1993 | Forte |
| 5,549,686 | A | 8/1996 | Johnson |
| 5,702,458 | A | 12/1997 | Burstein |
| 5,906,643 | A | 5/1999 | Walker |
| 5,964,808 | A | 10/1999 | Blaha |
| 6,013,103 | A | 1/2000 | Kaufman |
| 6,080,195 | A | 6/2000 | Colleran |
| 6,206,926 | B1 | 3/2001 | Pappas |
| 6,325,828 | B1 | 12/2001 | Dennis |
| 6,443,991 | B1 | 9/2002 | Running |
| 6,558,426 | B1 | 5/2003 | Masini |
| 6,726,723 | B2 | 4/2004 | Running |
| 7,160,330 | B2 | 1/2007 | Axelson |
| 7,326,252 | B2 | 2/2008 | Otto |
| 7,413,577 | B1 | 8/2008 | Servidio |
| 7,678,152 | B2 | 3/2010 | Suguro |
| 2004/0243244 | A1 | 12/2004 | Otto |
| 2004/0243245 | A1 | 12/2004 | Plumet |
| 2005/0192672 | A1 | 9/2005 | Wyss |
| 2005/0209701 | A1 | 9/2005 | Suguro et al. |
| 2006/0136066 | A1 | 6/2006 | Plumet |
| 2007/0135925 | A1 | 6/2007 | Walker |
| 2008/0097615 | A1 | 4/2008 | Lipman |
| 2008/0119940 | A1 | 5/2008 | Otto |
| 2008/0288080 | A1 * | 11/2008 | Sancheti ................. 623/20.24 |
| 2009/0306785 | A1 * | 12/2009 | Farrar et al. ............. 623/20.27 |
| 2009/0319048 | A1 | 12/2009 | Shah |
| 2009/0326667 | A1 * | 12/2009 | Williams et al. ......... 623/20.31 |
| 2010/0016979 | A1 | 1/2010 | Wyss |
| 2010/0036499 | A1 * | 2/2010 | Pinskerova ............... 623/20.31 |
| 2010/0161067 | A1 | 6/2010 | Saleh |

FOREIGN PATENT DOCUMENTS

| | | |
|---|---|---|
| DE | 69204201 T2 | 1/1996 |
| DE | 69906035 T2 | 1/2004 |
| DE | 69532047 T2 | 6/2004 |
| DE | 60216157 T2 | 9/2007 |
| DE | 202009012704 U1 | 12/2009 |
| EP | 0381352 | 8/1990 |
| EP | 0510299 | 10/1992 |
| EP | 0941719 | 9/1999 |
| EP | 1050283 | 11/2000 |
| EP | 1591082 | 11/2005 |
| GB | 2067412 | 7/1981 |
| GB | 2 253 147 A | 2/1992 |
| JP | 2004-166802 | 6/2004 |
| JP | 2005-261538 | 9/2005 |
| JP | 2006511278 | 4/2006 |
| WO | 2004058108 | 7/2004 |
| WO | 2007119173 | 10/2007 |
| WO | 2009105495 | 8/2009 |
| WO | WO-2010108550 A1 | 9/2010 |

OTHER PUBLICATIONS

Chandran, Nagarajan, et al., Optimisation of the Posterior Stabilised Tibial Post for Greater Femoral Rollback After Total Knee Arthroplasty—A Finite Element Analysis, International Oprthopedics (SICOT) (2009); vol. 33; pp. 687-693; Springer-Verlag 2008.

Churchhill, D. L., Ph.D., et al.; The Influence of Femoral Rollback on Patellofemoral Contact Loads in Total Knee Arthroplasty; The Journal for Arthroplasty; vol. 16, No. 7, 2001; pp. 909-918.

Kocmond, Jonathan H., M.S. et al.; Stability and Range of Motion of Insall-Burstein Condylar Protheses: A Computer Simulation Study; The Journal for Arthroplasty; vol. 10, No. 3, 1995; pp. 383-388.

Suggs, Jeremy F. et al.; Patient Function After a Posterior Stabilizing Total Knee Arthroplasty: Cam-Post Engagement and Knee Kinematics; Knee Surg Sports Traumatol Arthrosc (2008); vol. 16; pp. 290-296; Springer-Verlag 2007.

Tamaki, Masashi, M.D., et al.; In Vivo Kinematic Analysis of a High-Flexion Posterior Stabilized Fixed-Bearing Knee Prosthesis in Deep Knee-Bending Motion; The Journal of Arthroscopy; vol. 23, No. 6, 2008; pp. 879-885; Elsevier, Inc. 2008.

Walker, Peter S., Ph.D.; Design Features of Total Knees for Achieving Normal Knee Motion Characteristics; The Journal of Arthroscopy; vol. 24, No. 3; 2009; pp. 475-483; Elsevier, Inc. 2009.

Mihalko, William M, Ph.D. and Krackow, Kenneth A., M.D.; Posterior Cruciate Ligament Effects on the Flexion Space in Total Knee Arthroplasty; Clinical Orthopaedics and Related Research; Jul. 30, 1997; pp. 243-250; No. 360; Lippencott Williams & Wilkins, Inc.; 1999.

International Search Report for PCT/US2009/069163, mailed Jul. 5, 2010.

International Application Serial No. PCT/IB2012/002240, International Search Report and Written Opinion mailed Jan. 2, 2013, 6 pgs.

Japanese Office Action issued in Application No. 2011-542566, dated Nov. 14, 2013.

Japanese Final Office Action with translation issued in related Japanese Application No. 2011-542566, dated Jun. 18, 2014.

International Report on Patentability issued in related International Application No. PCT/IB2012/002240, dated May 14, 2014.

* cited by examiner

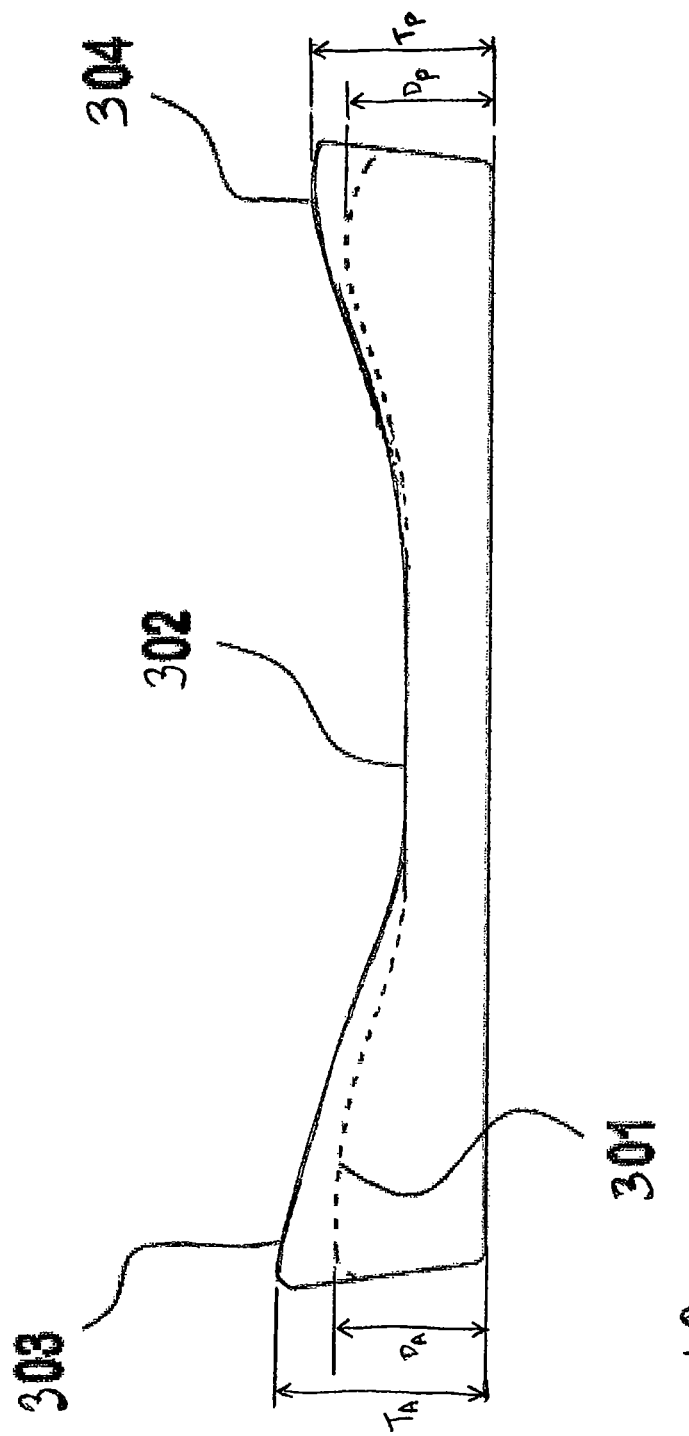

KNEE PROSTHESIS

This application is the U.S. National Phase application of PCT International Application No. PCT/US2009/069163, filed Dec. 22, 2009, which is a continuation-in-part of U.S. Non-provisional application Ser. No. 12/484,594, filed Jun. 15, 2009, which claims the benefit of priority of U.S. Provisional Application Ser. No. 61/140,183, filed Dec. 23, 2008, all of which are hereby fully incorporated by reference as if fully set forth herein.

FIELD OF INVENTION

The field of invention relates to artificial joints, and more particularly to knee prostheses.

BACKGROUND

As is the case with many joint prostheses or replacements, replicating natural anatomical movement through artificial mechanical devices proves challenging. This is true especially with the knee, which allows for relative complex movement and kinematics between the femoral condyles and the tibia. This relative motion is complex in that it accounts for both rolling and sliding between the contact surfaces at varying rates throughout the flexion arc. Along with such movement during knee bending is a rotational movement between the tibia and femur. As such, knee prostheses have historically tried to replicate the full range of knee movement, throughout and between full flexion and extension in all planes (coronal-varus/valgus, sagittal-flexion, transverse-rotation). True anatomical movement would allow rollback and translation of the femoral condyles on the tibia, all while also allowing rotational movement during flexion/extension.

Prior art designs have included femoral components with cams and tibial components with posts. It has been disclosed that an asymmetrical cam can be utilized to cause rotation between the two components. These designs, however, have taught architectures that require relatively high posts to support upward movement of the cam during flexion and/or rely on the anterior-posterior position of the post and cam. Other prior art designs have disclosed the use of tibial bearing surfaces to cause rotation between the components. These designs, however, have taught architectures that require tibial components that are asymmetrical in the lateral-medial cross-section.

SUMMARY OF INVENTION

The present invention identifies and overcomes a further shortcoming of the prior art. As stated above, true anatomical movement would allow rollback and translation of the femoral condyles on the tibia, all while also allowing rotational movement during flexion/extension. It has now been identified that knee prosthesis designs, which utilize bearing surfaces to allow flexion/extension and enable rotational movement, often exhibit a forward translation of the femoral component upon the tibial component. This phenomenon, called "paradoxical roll forward", prevents the knee prosthesis from accurately replicating the anatomic movement of a natural knee. Embodiments of the present invention prevent paradoxical roll forward and enable true anatomical movement of the knee.

The present invention provides a knee prosthesis having a femoral component with two condyles with an opening disposed between the two condyles. Also included is a tibial component having bearing surfaces to support each of the femoral component condyles. The femoral component and tibial component are engageable by contact between the femoral condyles and tibial bearing surfaces. By moving the femoral and tibial components in flexion from about 0° to about 165°, the contact regions between the femoral component and the tibial component cause rotation between the tibial and femoral components.

A natural knee contains a posterior cruciate ligament which helps provide stability and strength to the knee joint. This ligament may become damaged or ruptured and, thus, no longer provide support to the knee joint. The present invention provides prostheses which employ cruciate-substituting or cruciate-retaining knee prosthesis architectures for achieving kinematic knee motion. Embodiments of the present invention contain components which function to substitute for damaged or ruptured posterior cruciate ligament. Other embodiments of the present invention work to supplement the cruciate ligament when it is healthy enough to be retained in the knee prosthesis.

In one embodiment, the knee prosthesis includes a femoral component with two condyles with an opening disposed between the two condyles, and a cam extending between the condyles forming a posterior boundary to the opening. The knee prosthesis also includes a tibial component having bearing surfaces to support each of the femoral component condyles, and a post disposed between the bearing surfaces and extending superior from the tibial component. The femoral component and tibial component are engageable by contact between the femoral condyles and tibial bearing surfaces, and by contact between the cam and post during at least a portion of flexion between the femoral and tibial components. By moving the femoral and tibial components in flexion from about 45° to about 165°, the contact region between the cam and post moves inferiorly and medially to cause medial rotation between the tibial and femoral components.

In another embodiment, the knee prosthesis includes a femoral component with two condyles, with an opening disposed between the two condyles, and a tibial component having bearing surfaces to support each of the femoral component condyles. The medial and lateral femoral condyles are asymmetrical in an anterior-posterior cross-section. The lateral condyle has a similar architecture of the lateral condyle of the first embodiment, but the medial condyle of this embodiment has at least one region of uniform radius. Similarly, the medial and tibial bearing surfaces are asymmetrical in an anterior-posterior cross-section. The femoral component and tibial component are engageable by contact between the femoral condyles and tibial bearing surfaces. However, the lateral and medial bearing surfaces remain symmetrical in the lateral-medial cross-section. During flexion of the femoral and tibial components from about 0° to about 90°, a period of flexion in which other knee designs are prone to paradoxical roll forward, an anterior lip of the medial tibial bearing surface functions to prevent roll forward of the femoral component of the present knee prosthesis. The anterior-posterior design architecture of the medial tibial bearing surface constrains the translation of the femoral component and works with the uniform radius of curvature of the medial femoral condyle to also prevent the paradoxical roll forward. The asymmetrical lateral and medial femoral condyles, and the asymmetric lateral and medial tibial bearing surfaces enable the condyles to translate posteriorly at different rates and cause rotation between the tibial and femoral components. Thus, by moving the femoral and tibial components in flexion from about 0° to about 165°, the contact regions between the femoral component and the tibial component prevent roll forward, enable roll back, and cause rotation between the tibial and femoral components.

BRIEF DESCRIPTION OF THE FIGURES

FIG. 18a illustrates an anterior-posterior cross-sectional view of a tibial component in accordance with another embodiment of the present invention;

FIG. 18b illustrates a reverse view of the anterior-posterior cross-sectional view of FIG. 18a;

DETAILED DESCRIPTION OF THE INVENTION

Figure 1:
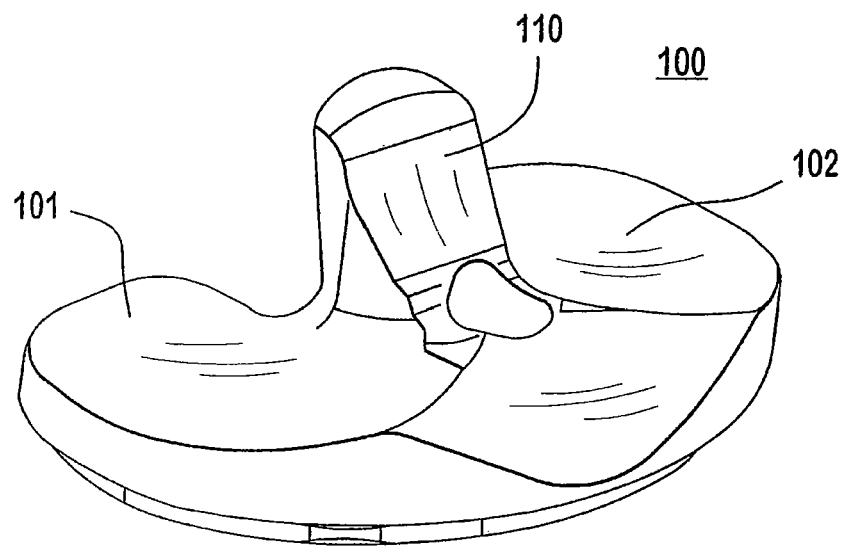
FIG. 1 illustrates a tibial component in accordance with an embodiment of the present invention.

The present invention provides a knee prosthesis which allows for anatomically correct knee movement. It does so by providing an upper, or femoral, component which is designed to mechanically interact with a lower, or tibial, component to achieve kinematic movement consistent with a natural knee joint. Generally, the two pieces interact by providing several different contact surfaces, not all of which are engaged between the two components of the knee throughout the range of motion.

Two such contact surfaces are the load bearing condylar surfaces between the femoral component and the tibial component. These surfaces are defined by medial and lateral condylar surfaces which are referred to as the load bearing surfaces for a given knee joint. Specifically, a medial load bearing surface is defined between the medial femoral condyle and its counterpart on the tibial component, namely a medial tibial accommodating surface. Likewise, a lateral load bearing surface is defined between the lateral femoral condyle and its counterpart on the tibial component, namely a lateral tibial accommodating surface.

In one embodiment of the present invention, a different contact surface also exists to cause rotational movement between the femoral and tibial components, during certain degrees of knee extension/flexion which will allow for a kinematic pattern that more closely resembles that of the natural knee. This contact surface is defined by interaction between a post on the tibial component (preferably polyethylene) and a cam surface on the femoral component (preferably metallic). Because the point of contact between the femoral condyles and their corresponding tibial load-receiving components changes in an anterior/posterior direction (that is to say there is front/back translation of the point of contact) during knee movement, the post and cam do not interact during all degrees of knee flexion. Instead, the post and cam only interact during those points of knee movement for which they are designed to cause a replicated natural knee kinematic envelop. This interaction occurs when the anterior/posterior movement of the femoral/tibial contact causes the post and cam to engage, or when flexion of the knee causes enough rollback of the femoral component to engage the tibial post against the cam of the femoral component.

It should be noted, however, that once flexion typically reaches about 45°, anterior/posterior translation does not stop but occurs at different rates in the medial and lateral compartments of the knee. Moreover, as the knee bends, the lateral condyle rolls back to a position of about 10-15 mm posterior at about 120° flexion, but the medial condyle rolls back only about 4-5 mm to a final position of about 1-3 mm posterior. This difference in posterior movement in the two compartments of the knee is seen as rotation of the femoral component on the tibial component, and occurs with continued rollback of the femoral condyles. This interaction of the post and cam, as well as the movement of the femoral condyles with respect to the tibial bearing surfaces will be addressed below.

The movement described is achieved through the present invention's architecture of the both the femoral component, the tibial component, and in particular the cam and post dimensions. All of these aspects are integrated into a system which provides for sophisticated, anatomical movement within the prosthetic knee of the present invention.

FIG. 1 shows a tibial component 100 in accordance with the present invention. This tibial component 100 has two load bearing surfaces, shown as load bearing surface 101 and load bearing surface 102. For a right knee joint, load bearing surface 101 would be the lateral condyle load bearing surface, and load bearing surface 102 would be the medial condyle load bearing surface. Post 110 is shown extending upward, or in a superior direction, from the lateral plane generally defining the tibial insert. Post 110 will be described in more detail below.

Figure 2:
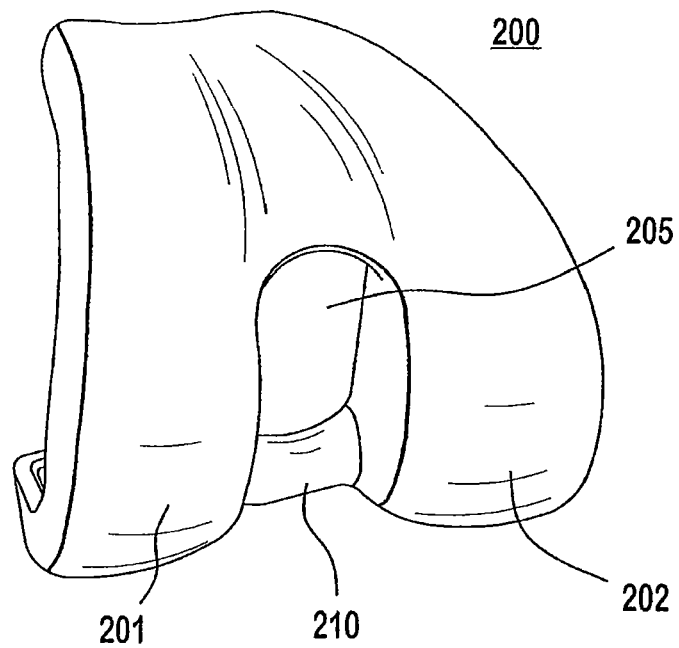
FIG. 2 illustrates a femoral component in accordance with an embodiment of the present invention.

FIG. 2 illustrates a femoral component 200 in accordance with the present invention. Cam 210 is shown bridging a gap between the femoral condyles 201 and 202. Opening 205 is defined by the condyles 201 and 202 which extend anteriorly around the side of the opening opposite cam 210. Cam 210 is generally disposed in a posterior portion of the opening in the femoral component. Cam 210 and its dimensions will be defined in more detail below.

Figure 3:
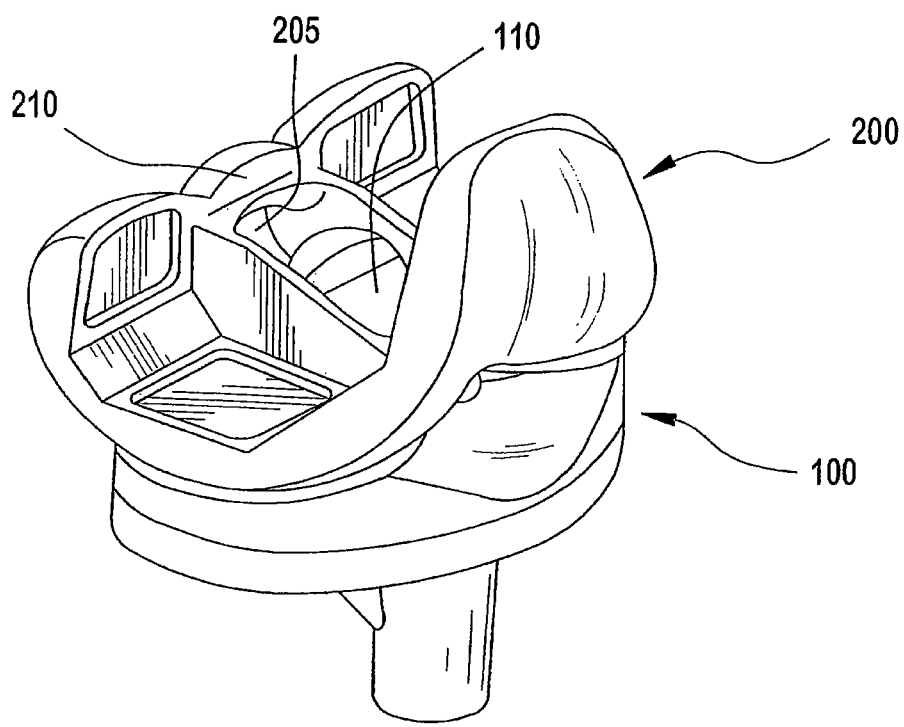
FIG. 3 illustrates a tibial component (with a stem) and a femoral component mated in accordance with an embodiment of the present invention.
Figure 4:
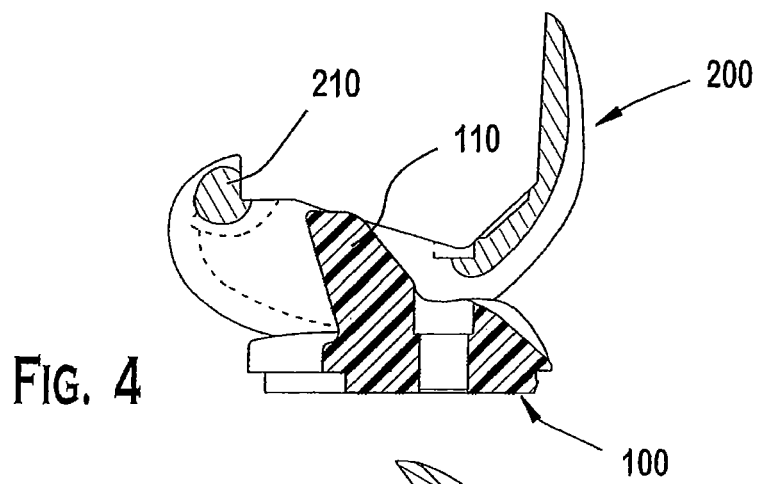
FIG. 4 illustrates a partial cross-sectional view of the prosthesis of an embodiment of the present invention at about 0° flexion.

FIG. 3 shows femoral component 200 disposed atop tibial component 100. Post 110 is shown extending through opening 205. FIG. 3 shows the components in a position of 0° flexion. As can be seen from FIG. 3, cam 210 is not in contact with post 110 at this point. It is also noteworthy that in this position, there is no contact between the anterior surface of post 110 and the anterior boundary of opening 205. This aspect can be seen perhaps more clearly in FIG. 4, which shows a partial cross-sectional view of that shown in FIG. 3. This aspect of the present invention is important because it reduces wear on the tibial post 110.

For an example of an implant having both anterior and posterior cams, see U.S. Pat. No. 6,325,828, which illustrates a femoral component having a blind hole or slot/recess (as opposed to an opening) bordered by cams on both sides (anterior and posterior) As such, and as explicitly disclosed, the anterior cam engages the post at full extension (or 0° flexion).

Figure 5:
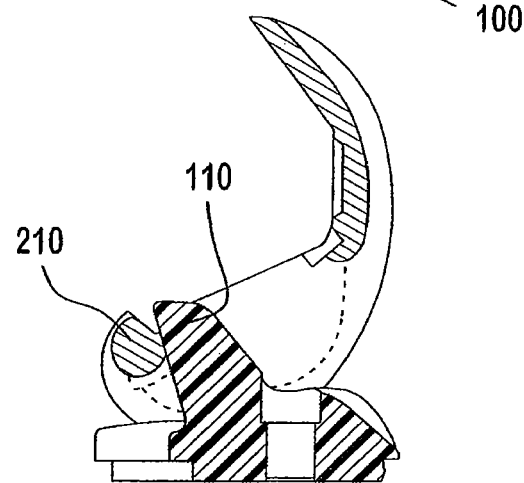
FIG. 5 illustrates a partial cross-sectional view of the prosthesis of an embodiment of the present invention at about 45° flexion.

As the knee bends toward a flexion of about 45°, cam 210 moves toward post 110 as anterior translation occurs between the contact region of the femoral condyles and their respective load bearing surfaces on tibial component 100. The orientation of the two components, and in particular the cam and post, at 45° flexion, is illustrated in FIG. 5, which shows a partial cross-sectional view of the components at about 45° flexion. At this point in the knee movement, the cam 210 has contacted post 110 and as further flexion occurs, the rotational movement caused by the interaction of the post and cam causes slight medial rotation of the femoral component with respect to the tibial component.

Figure 6:
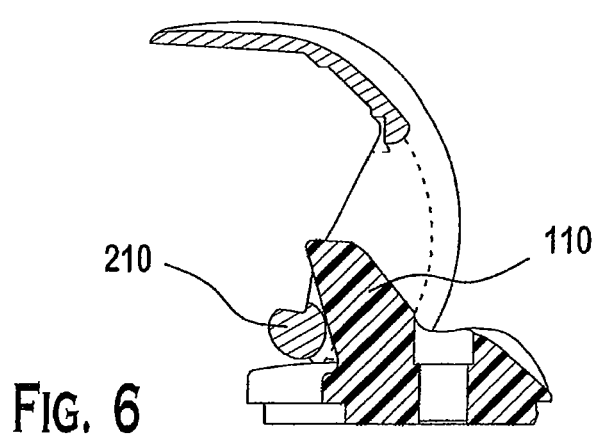
FIG. 6 illustrates a partial cross-sectional view of the prosthesis of an embodiment of the present invention at about 90° flexion.

FIG. 6 shows the partial cross-section of the two components at about 90° flexion. Note that the contact point between the cam and post moves downward along the post, or inferiorly, as flexion increases. This is due to the architecture of the cam and post and is designed as a part of the knee movement based on the anatomical requirements of the natural knee joint.

Figure 7:
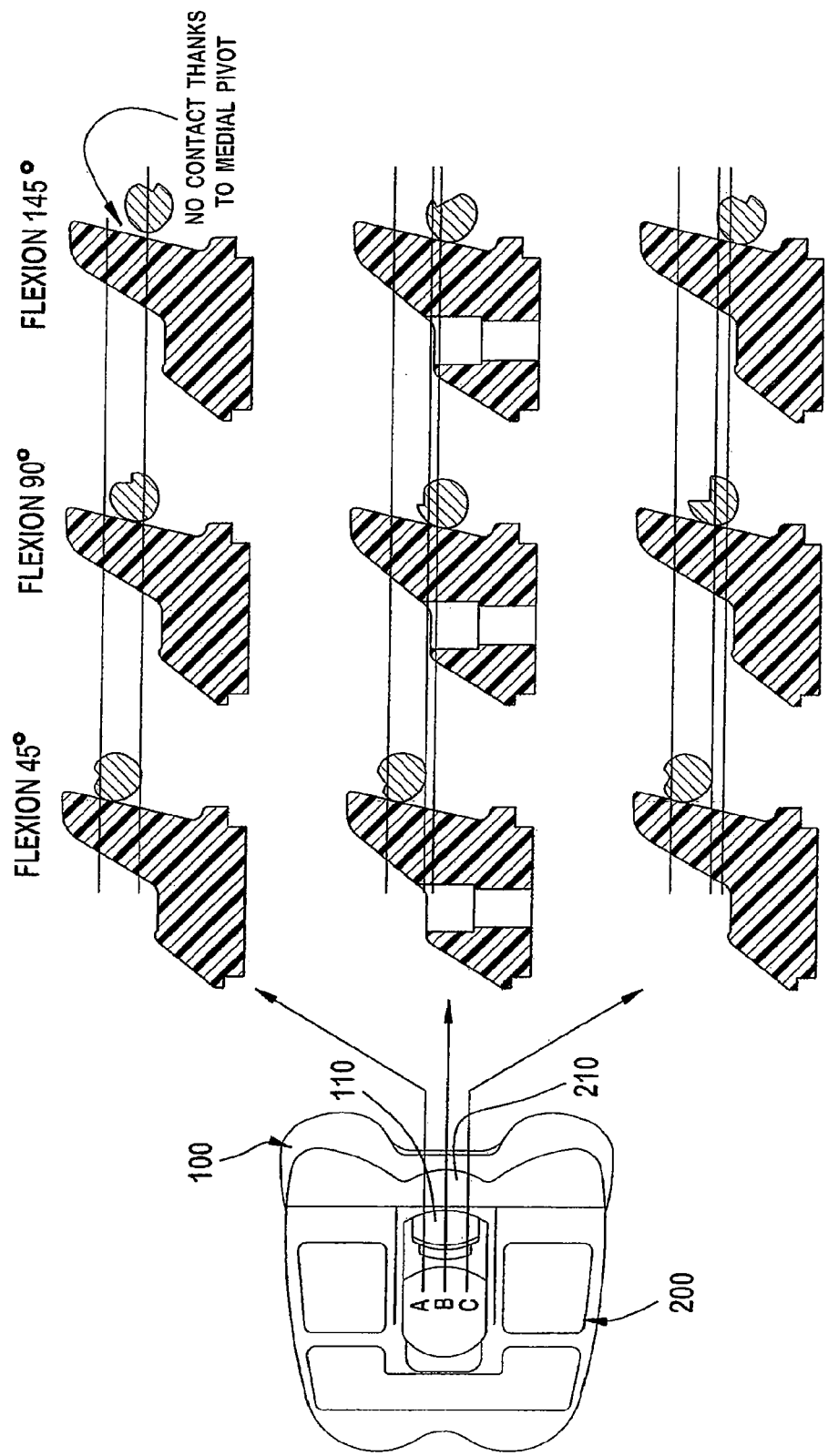
FIG. 7 illustrates a series of cross-sectional views at three planes of interaction of the cam and post in accordance with an embodiment of the present invention.

Further defining this aspect of the invention is FIG. 7. FIG. 7 shows the cross-sections of three different planes at three different angles of flexion. Planes A, B, and C are shown and illustrate the asymmetry of the cam 210 and the effect of that asymmetry on the rotation and inferior movement of the cam down the post as flexion increases. At 45° flexion, plane A indicates contact of the cam and post at a point relatively high on the post. As flexion increases to 90°, the cam is working its way down the post as the femoral component rotates medially with respect to the tibial component. At 145° flexion, not only has the cam moved further downward along the posterior side of the post (at planes B and C), but in fact, at plane A, or the lateral side of the cam, the cam has disengaged the post altogether as medial rotation has separated the cam from the post at this point. Thus, there is seen a medial rotation consistent with natural knee movement while the cam has actually moved down along the post. Stability is one advantage of the implant designed this way in accordance with the invention.

Figure 8:
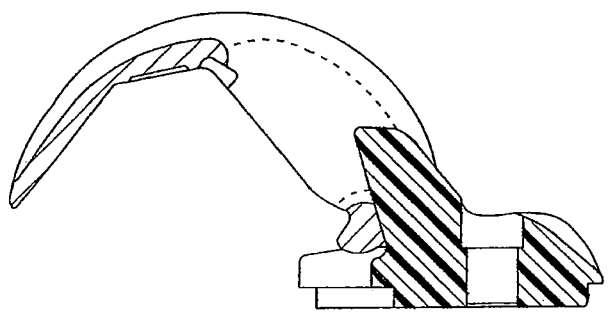
FIG. 8 illustrates a partial cross-sectional view of the prosthesis of an embodiment of the present invention at about full flexion.

This later point is important to achieve natural knee movement with respect to a patellar implant. FIG. 8 shows knee prosthesis of the present invention at about 145° flexion. At this point, and as noted above, the cam has moved downward along the post. The post therefore only needs to be as high as is necessary to engage the cam at the first point of contact, namely at about 45° flexion (because after that the cam moves downward).

Figure 9:
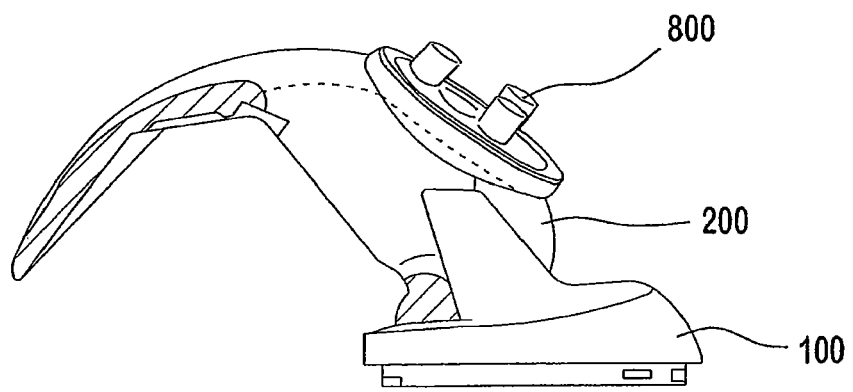
FIG. 9 illustrates that of FIG. 8 but with the addition of a patellar implant.

The relative shortness of the post is important because it allows for clearance of the patellar implant as shown in FIG. 9. There, patellar implant 800 is shown disposed cm femoral component 200. Unlike prior art designs that have upward cam movement during flexion, and therefore require higher posts to extend upward from the initial point of contact, the present invention is configured to provide downward cam movement and therefore relatively shorter posts are necessary. This allows for patellar clearance during knee rotation as shown in FIG. 9.

Figure 10:
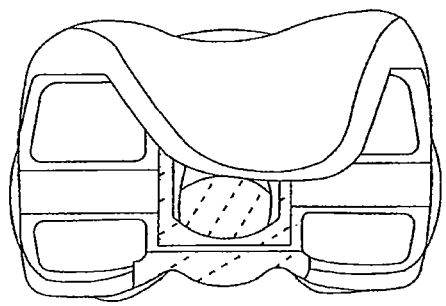
FIG. 10 illustrates a top down view of the prosthesis of an embodiment of the present invention at about 45° flexion.
Figure 11:
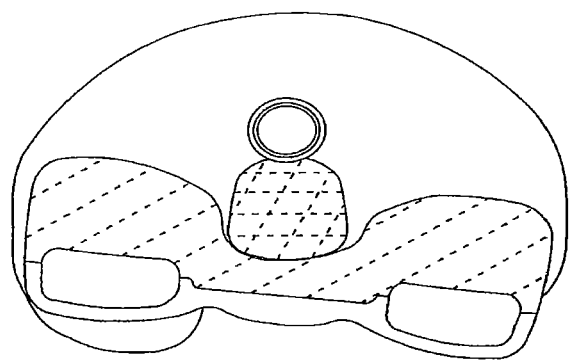
FIG. 11 illustrates a partial cross-sectional view from the top down of the prosthesis of an embodiment of the present invention at about 90° flexion.
Figure 12:
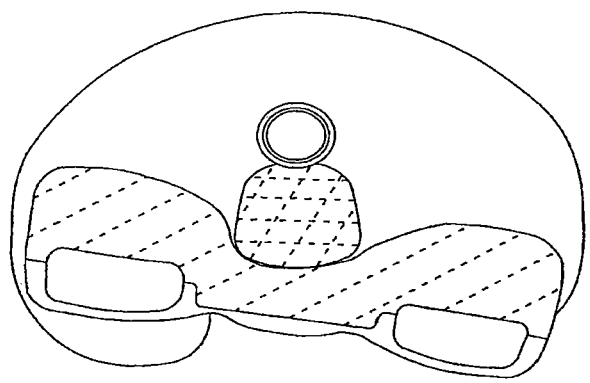
FIG. 12 illustrates a partial cross-sectional view from the top down of the prosthesis of an embodiment of the present invention at about 145° flexion.

By way of further illustration, FIGS. 10-12 show a top-down partial cross-sectional view of the prosthesis during flexion of 45°, 90°, and 145°, respectively. As can be seen from these views, the cam has a shape and size quite different on the lateral side than on its medial side. This cam and its particular shape and orientation provides an angled surface which acts with the post to drive a very precise medial pivot and femoral rotation in the transverse plane.

Figure 13:
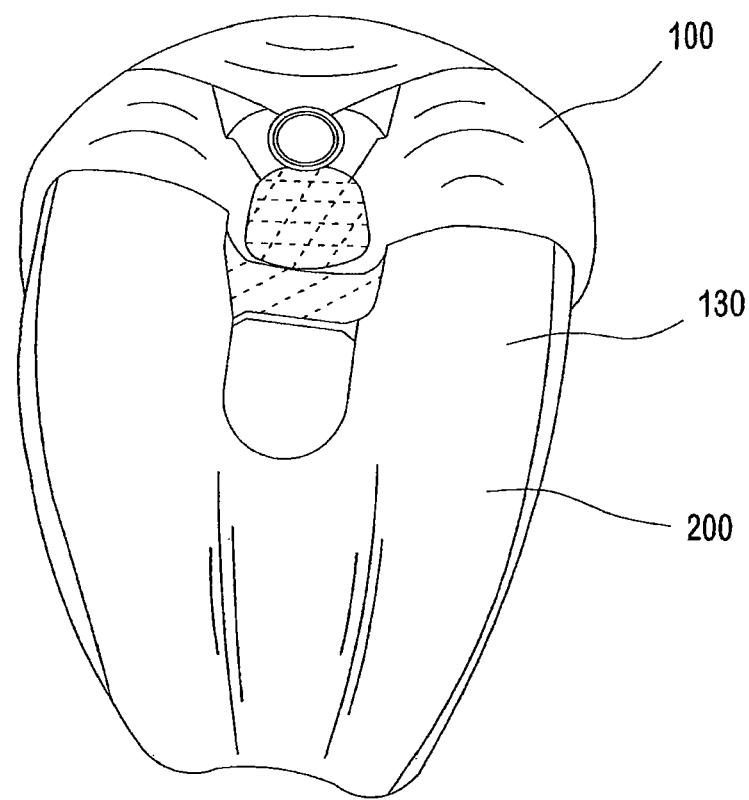
FIG. 13 illustrates a top down view of the prosthesis of an embodiment of the present invention at about 145° flexion.

FIG. 13 illustrates a top down view of the cam and post interaction and also shows the medial rotation of the femoral component with respect to its tibial component. Note that even at this relatively high flexion, the cam is disposed somewhat under the post and enlarges in cross-sectional area toward the lateral end of the cam where it abuts the lateral condyle 130.

Figure 14:
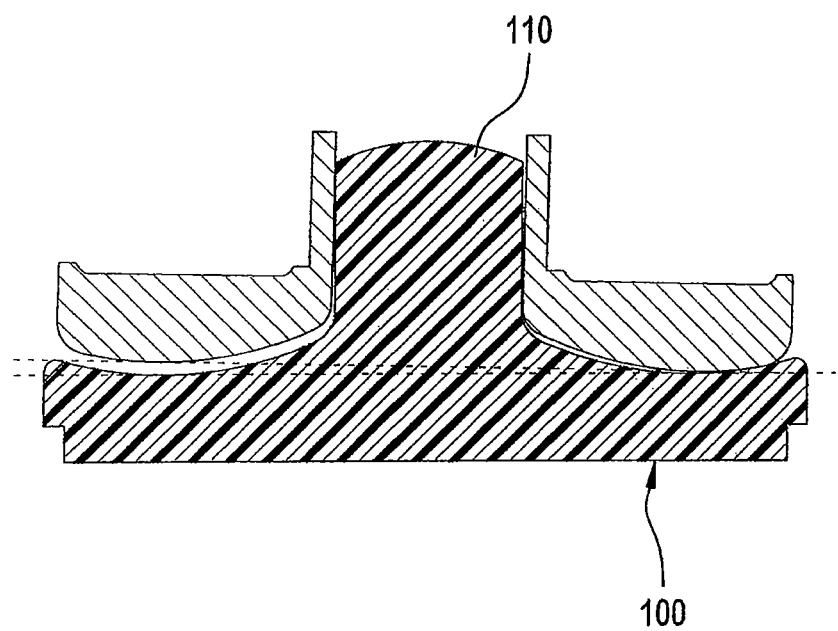
FIG. 14 illustrates a cross-sectional view at high flexion showing separation of the lateral condyle from tibial component in an embodiment of the present invention.

It is also noteworthy that the post of the present invention may be sized to permit or restrict separation of the lateral condyle from the tibial component, which may occur due to varus-valgus moments and may be necessary to replicate a natural knee movement. See, for example, FIG. 14, which shows separation of the lateral condyle 140 from tibial component 100. This separation is due, in part, to the architecture of the cam and the post to which it engages during flexion. FIG. 14 shows an embodiment of the present invention featuring an optional increased post width design in the medial direction, which can be used to support varus-valgus moments. The post width can be sized to resist such varus-valgus motion between the femoral and tibial components, such as in the case of diminished soft tissue strength in the knee joint. In such cases, the post can be sized to provide additional strength and support to the knee joint. Conversely, the post width can be sized to allow some degree of varus-valgus motion to replicate anatomically correct movement.

One advantage to the prosthesis of the present invention is that it allows for less soft tissue strain by allowing for more anatomical movement instead of equal rollback in both compartments of the tibial insert. This design gives three advantages over previous designs: 1) less soft tissue strain due to more anatomical movement, 2) better natural motion replication in the medial compartment without increasing constraint, and 3) decreased tibial strain with no edge loading in the medial compartment. Although the above illustrations show knee flexion at 0°, 90°, and 145°, the range of motion allowed for in the design would be at least −10° (hyperextension) to about 165° (high flexion) with supported articulation in the medial and lateral compartments of the knee.

Moreover, as flexion continues beyond 45°, anterior/posterior translation continues to occur, but is guided by the post/asymmetric-cam interaction. Because of the relative dimensions of the post, and in particular the type of asymmetrical cam on the femoral component, proper rotational movement between the femoral component and tibial component is achieved.

Consistent with that described above, the interaction between the tibial component post and the femoral component tapered asymmetric cam, is designed to preferably begin at 45° flexion. It should be noted that the interaction can be controlled through manipulation of the dimensions of the post and cam. This is accomplished through varying the cross-sectional dimensions of the cam from a medial to lateral direction, with the lateral portion of the cam being generally larger than the medial portion. More specifically, the largest cross-sectional area of the cam occurs where the cam meets the lateral condyle. Moving in a medial direction, the cam tapers in a manner consistent with that which causes kinematic rotation as the knee bends past 45° flexion.

It is also noteworthy that there is no interaction between the post and cam at full extension. This prevents unnecessary wear on the tibial post which would otherwise weaken it over time and could even result in failure (i.e, it could shear off).

It has been identified that existing knee prosthesis designs, which utilize bearing surfaces to allow flexion/extension and enable rotational movement, exhibit a paradoxical roll forward of the femoral component upon the tibial component. This forward translation is unlike the anatomic movement of a natural knee. Embodiments of the present invention prevent such paradoxical roll forward and enable true anatomical movement of the knee.

In one such embodiment of the present invention, rotational movement between the femoral and tibial components is enabled by contact surface interaction between asymmetrical medial and lateral femoral condyles and their respective asymmetrical medial and lateral tibial bearing surfaces. In this embodiment, the lateral and medial condyles of the femoral component are asymmetrical such that the medial femoral condyle has at least one region of uniform radius and the lateral femoral condyle does not. For example, the lateral femoral condyle of this embodiment may be similar to the lateral femoral condyle of the embodiment described above with regard to FIGS. 1-14, while the medial femoral condyle has a different architecture. Correspondingly, the lateral and medial bearing surfaces of the tibial component are also asymmetrical in this later embodiment. The anterior and posterior lips of the medial tibial bearing surface project higher from the tibial component than the anterior and posterior lips of the lateral tibial bearing surface, creating asymmetry of the tibial component. However, the lateral and medial bearing surfaces remain symmetrical in the lateral-medial cross-section. This can be seen, for example, in FIG. 17.

During flexion of the femoral and tibial components from about 0° to about 90°, the anterior lip of the medial tibial bearing surface and a first region of uniform radius of curvature of the medial femoral condyle function to retain the medial femoral condyle at an effectively constant contact point upon the medial tibial bearing surface. This architecture further prevents roll forward of the medial femoral condyle on the medial tibial bearing surface. The lateral tibial bearing surface is less constrained in the anterior-posterior architecture to allow roll back to occur at an earlier degree of flexion than upon the medial tibial bearing surface. While the higher lips of the medial tibial bearing surface cause it to be asymmetrical with the lateral tibial bearing surface, the tibial component remains symmetrical in its minimum thickness along a medial-lateral cross-section. This minimum thickness symmetry of the tibial component allows the contact points of the medial and lateral condyles with their respective bearing surfaces, at 0° flexion, to be at equal elevations from the bottom of the tibial component. This is detailed further, for example, in FIGS. 17, 18a, and 18b. The medial lips retain the medial condyle within this area of the tibial bearing surface having symmetrical thickness during flexion from about 0° to about 90°. The point of contact between the femoral condyles and their corresponding tibial load-receiving components changes in an anterior/posterior direction (that is to say there is front/back translation of the point of contact) during knee movement. However, the asymmetrical structures of the lateral femoral condyle and lateral tibial bearing surface (vis-à-vis their respective medial counterparts) allow the lateral condyle to posteriorly translate upon the lateral bearing surface further. This disparity in posterior translation of the lateral and medial condyles is seen as rotation of the femoral component on the tibial component. Rotational movement, posterior translation, and other kinematic motion of this embodiment is therefore achieved without a femoral cam, a tibial post, or a post/cam contact surface. This novel functionality of this embodiment of the present invention is useful in knee replacement procedures, especially in cruciate-retaining procedures where such functionality has not been possible prior to the present design.

Once flexion reaches about 90°, anterior/posterior translation of the condyles does not stop but occurs at a different rate in the medial and lateral compartments of the knee. During deep flexion from about 90° to about 120°, a second region of uniform radius of the medial femoral condyle may be utilized to engage the anterior lip of the medial tibial bearing surface. Similarly, a third region of uniform radius of the medial femoral condyle can be used to engage the tibial component from about 120° to about 165° of flexion. These regions of uniform radius further enable rollback of the femoral condyles and rotation of the femoral component on the tibial component. Thus, by moving the femoral and tibial components in flexion from about 0° to about 165°, the contact regions between the femoral component and the tibial component prevent roll forward as well as cause rotation between the tibial and femoral components.

Figure 15:
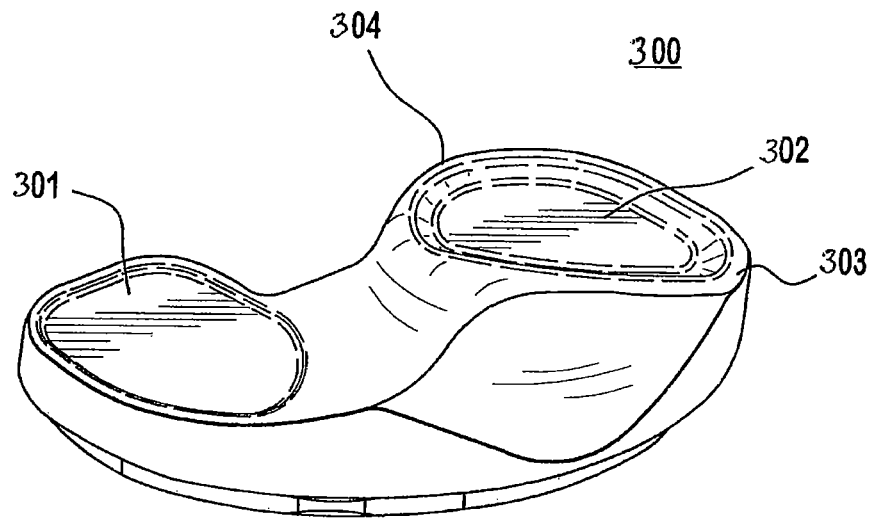
FIG. 15 illustrates a tibial component in accordance with another embodiment of the present invention.

FIG. 15 shows a tibial component 300 in accordance with an embodiment of the present invention. This tibial component 300 has two load bearing surfaces, shown as load bearing surface 301 and load bearing surface 302. For a right knee joint, load bearing surface 301 would be the lateral condyle load bearing surface, and load bearing surface 302 would be the medial condyle load bearing surface. Anterior lip 303 and posterior lip 304 project from medial condyle bearing surface 302, Anterior lip 303 and posterior lip 304 are defined in more detail below.

Figure 16:
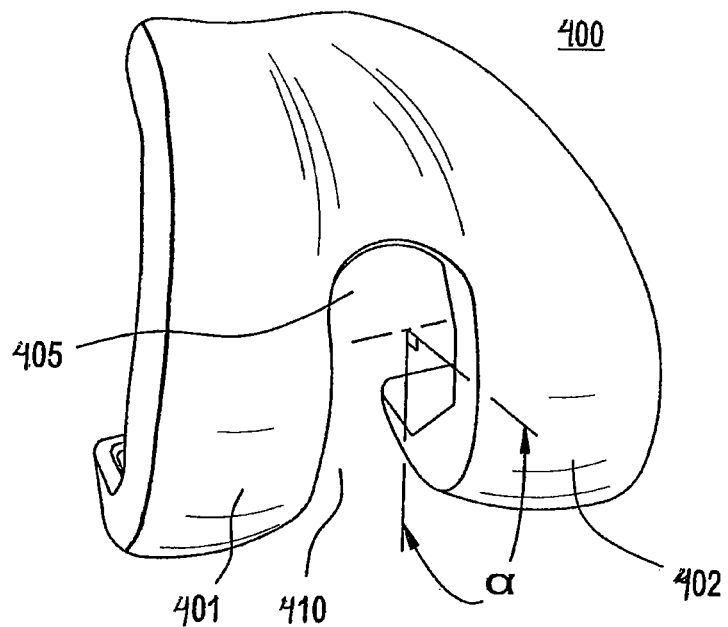
FIG. 16 illustrates a femoral component in accordance with another embodiment of the present invention.

FIG. 16 illustrates a femoral component 400 in accordance with an embodiment of the present invention. Opening 410 is defined by the condyles 401 and 402 which extend anteriorly around the side of the opening 410. In this illustration, condyle 401 is the lateral femoral condyle and condyle 402 is the medial femoral condyle. Condyles 401 and 402 are defined in more detail below.

Figure 17:
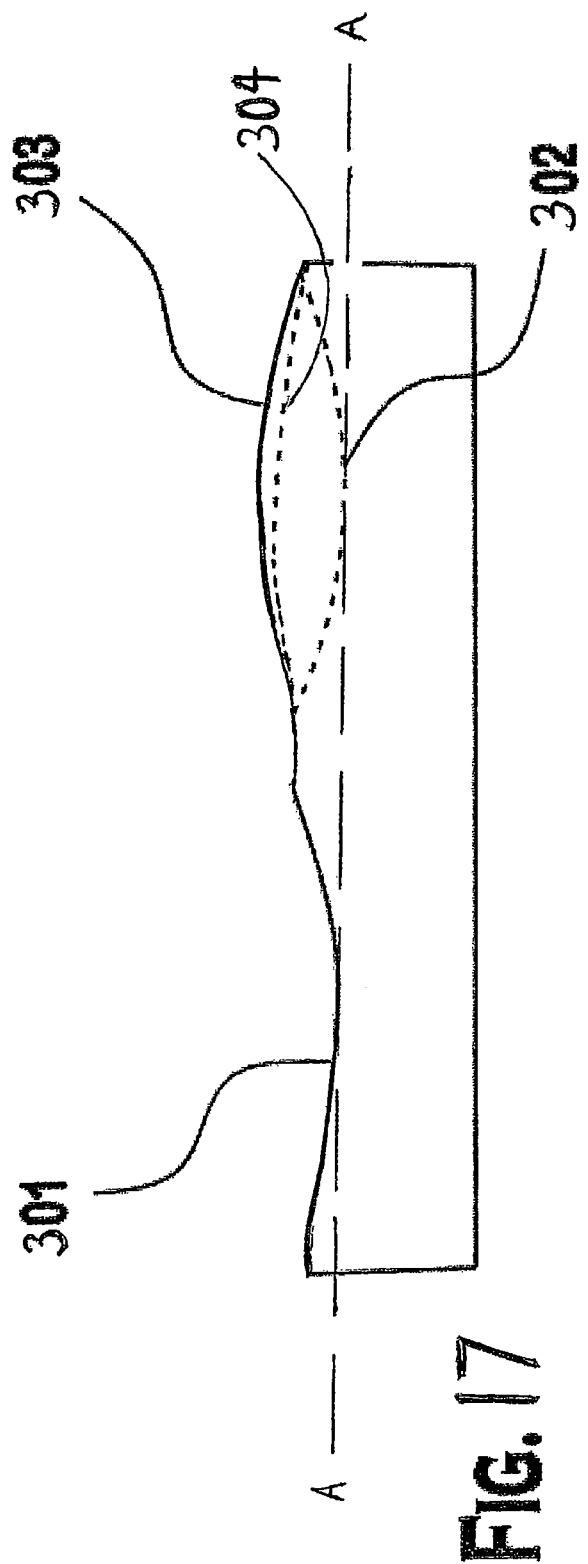
FIG. 17 illustrates a lateral-medial cross-sectional view of a tibial component in accordance with another embodiment of the present invention.

FIG. 17 illustrates a lateral-medial cross-sectional view of a tibial component in accordance with this embodiment of the present invention. Line "A" of FIG. 17 shows that the lateral and medial bearing surfaces 301 and 302, respectively, are symmetrical and of equivalent thickness (or, elevation) from the bottom of the tibial component. Anterior lip 303 and posterior lip 304 of the medial bearing surface 302 show the asymmetrical architecture of the tibial component, vis-à-vis the lateral side of the tibial component. This can also be seen in FIG. 15. In this embodiment of the present invention, at about 0°, the medial and lateral femoral condyles would engage the tibial component at bearing surfaces 301 and 302, at contact points along line "A" (shown in FIG. 17). As the knee bends in flexion from about 0° to about 90°, an anterior lip 303 of the medial tibial bearing surface 302 functions to retain the medial femoral condyle at an effectively constant contact point upon the tibial bearing surface and interacts with a region of the medial femoral condyle having a uniform radius of curvature to prevent roll forward of the femoral component. The architecture of the lateral tibial bearing surface does not contain this constraint and engages the non-uniform radius of the lateral femoral condyle to enable roll back.

Figure 18B:
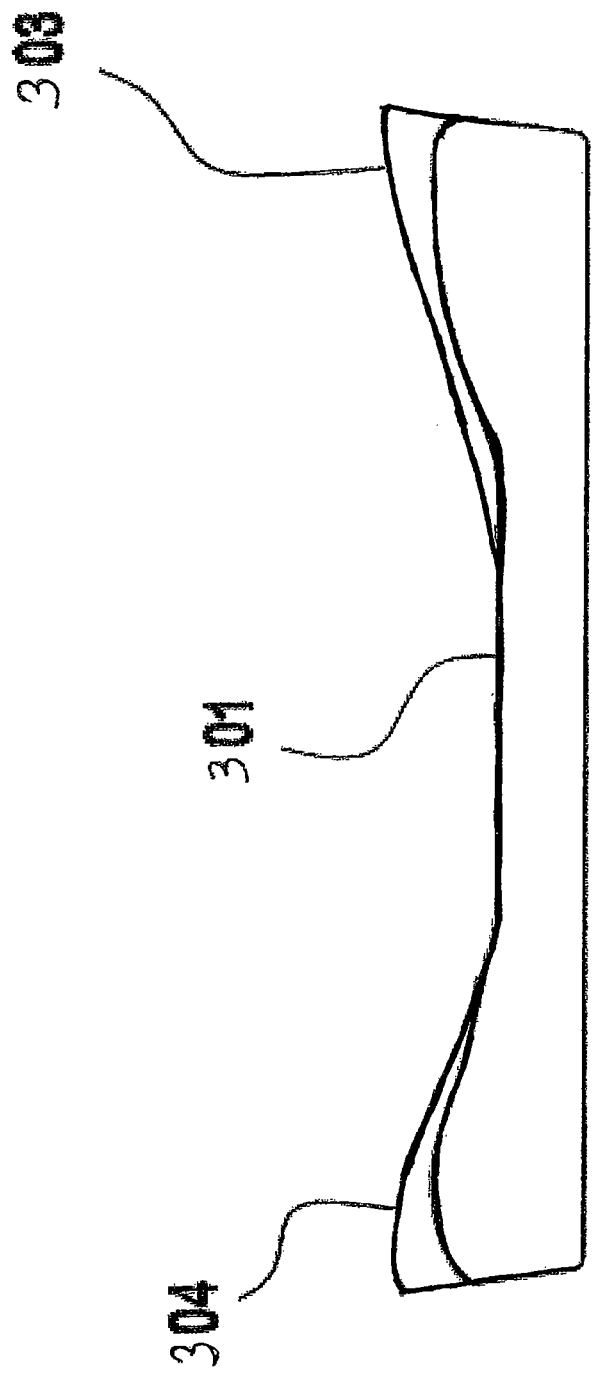

FIG. 18a illustrates an anterior-posterior cross-sectional view of a tibial component in accordance with this embodiment of the present invention, while FIG. 18b illustrates a reverse view of this same cross-section. The medial tibial bearing surface 302 has projections extending superiorly from the tibial component which comprises an anterior lip and a posterior lip. Anterior lip 303 has a thickness $T_A$ and posterior lip 304 has a thickness $T_P$. In one embodiment of the present invention, thicknesses $T_A$ and $T_P$ have a proportional ratio of about 7:3. The lateral tibial bearing surface 301 has an anterior lip dimension $D_A$, and a posterior lip dimension $D_P$. In one embodiment of the present invention, dimensions $D_A$ and $D_P$ have a proportional ratio of about 4:2. As detailed, the medial bearing surface 302 includes higher lip projections than the lateral bearing surface 301. In this example, the anterior lips of the medial and lateral bearing surfaces have about a 7:4 ratio while the posterior lips have about a 3:2 ratio.

Figure 19A:
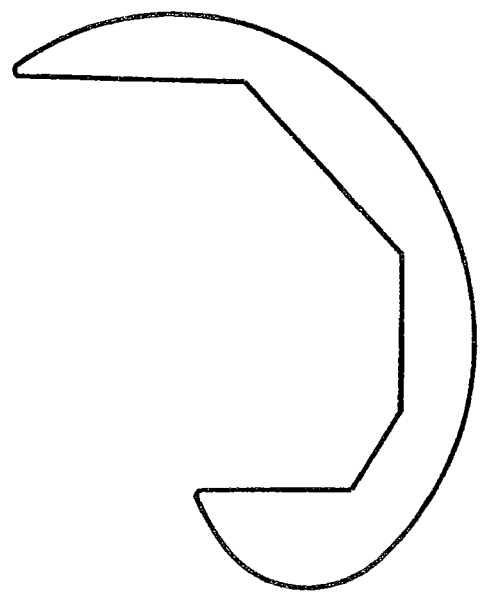
FIG. 19a illustrates a partial cross-sectional view of a medial femoral condyle of another embodiment of the present invention at about 0° flexion.
Figure 19B:
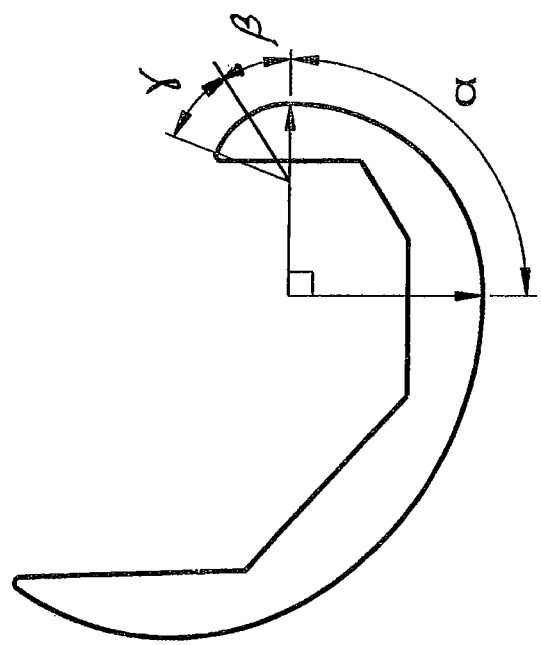
FIG. 19b illustrates a partial cross-sectional view of a lateral femoral condyle of another embodiment of the present invention at about 0° flexion.

FIG. 19a and FIG. 19b illustrate partial cross-sectional views of the medial femoral condyle and the lateral femoral condyle, respectively, of another embodiment of the present invention at about 0° flexion. The architecture of the lateral femoral condyle has a changing radius at its distal end, while the medial femoral condyle has at least one region of uniform radius at its distal end. In the embodiment shown in FIG. 19a, the medial condyle has a first region of uniform radius α, a second region of uniform radius β, and a third region of uniform radius γ. The lateral condyle is asymmetrical from the medial condyle in that it does not possess some or all of these regions of uniform radius, as is shown in FIG. 19b.

During flexion of the femoral and tibial components from about 0° to about 90°, the contact point between the femoral and tibial components is in this first region of uniform radius α. This uniform radius design of the medial condyle combines with the anterior lip architecture of the medial bearing surface to prevent roll forward of the femoral component of the present knee prosthesis. Additionally, the asymmetrical lateral and medial femoral condyles, and the asymmetric lateral and medial tibial bearing surfaces enable the condyles to translate posteriorly at different rates and cause rotation between the tibial and femoral components. Optionally, the medial condyle may include a second region of uniform radius β to engage the medial bearing surface in flexion from about 90° to about 120°, and a third region of uniform radius γ to engage the medial bearing surface in flexion from about 120° to about 165°. The second region of uniform radius β and third region of uniform radius γ may assist further in the purposes of this invention. Thus, by moving the femoral and tibial components in flexion from about 0° to about 165°, the contact regions between the femoral component and the tibial component prevent roll forward, enable roll back, and cause rotation between the tibial and femoral components.

Figure 20:
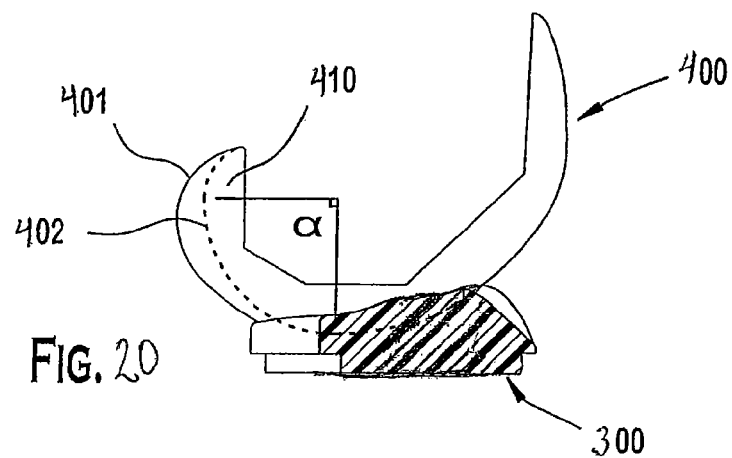
FIG. 20 illustrates a partial cross-sectional view of the prosthesis of another embodiment of the present invention at about 0° flexion.
Figure 21:
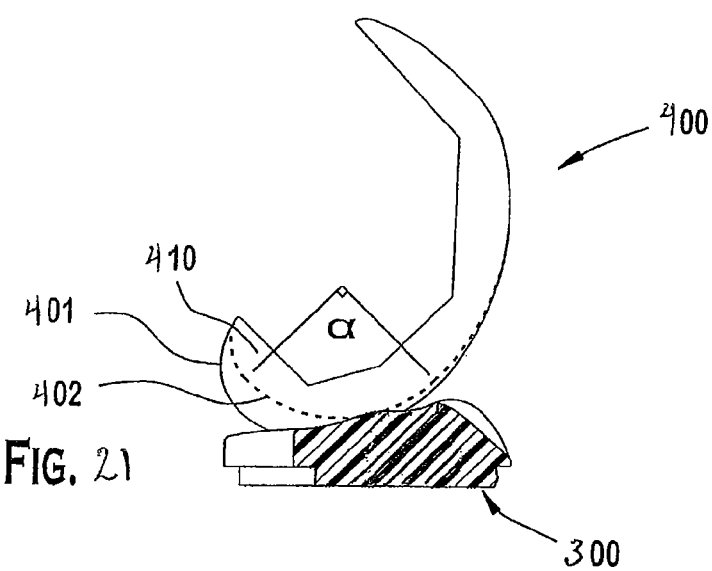
FIG. 21 illustrates a partial cross-sectional view of the prosthesis of another embodiment of the present invention at about 45° flexion.
Figure 22:
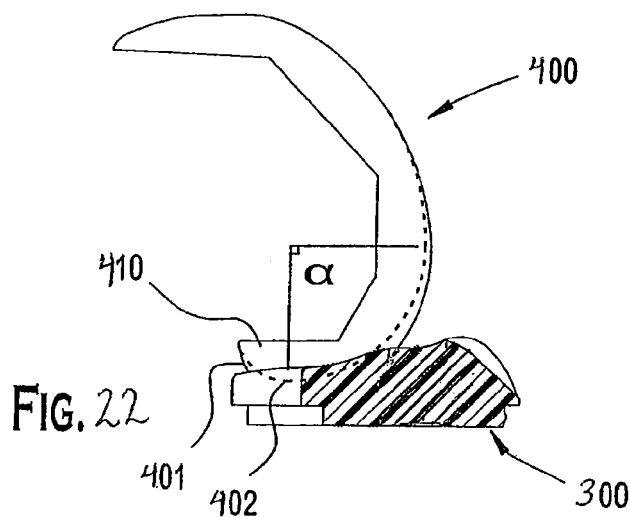
FIG. 22 illustrates a partial cross-sectional view of the prosthesis of another embodiment of the present invention at about 90° flexion.
Figure 23:
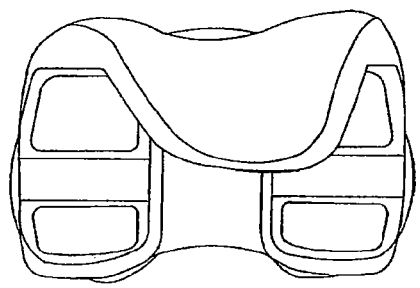
FIG. 23 illustrates a top down view of the prosthesis of another embodiment of the present invention at about 45° flexion.
Figure 24:
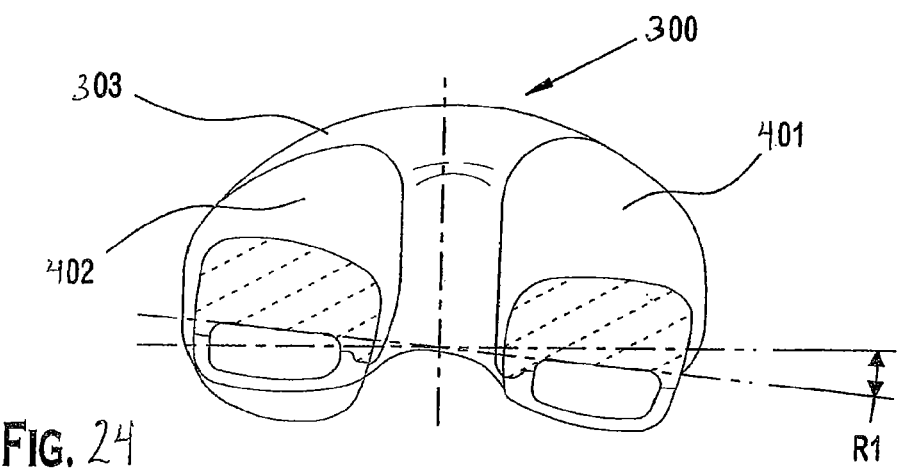
FIG. 24 illustrates a partial cross-sectional view from the top down of the prosthesis of another embodiment of the present invention at about 90° flexion.
Figure 25:
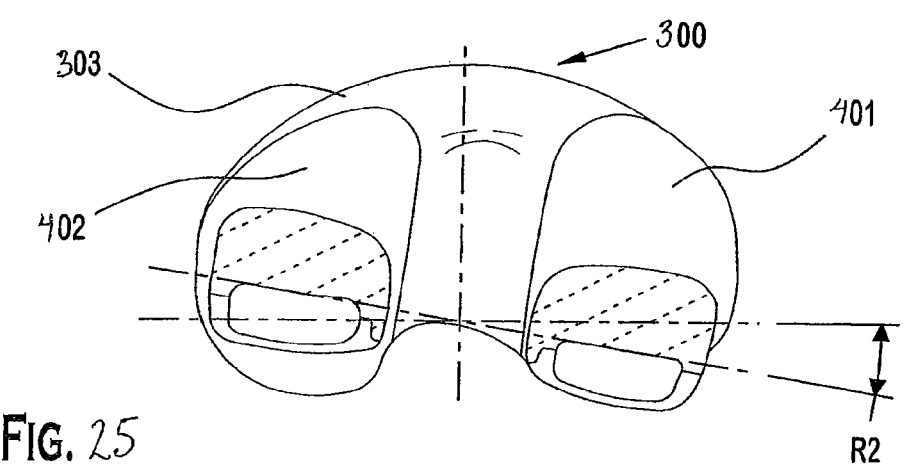
FIG. 25 illustrates a partial cross-sectional view from the top down of the prosthesis of another embodiment of the present invention at about 145° flexion.

The interaction of the femoral condyles with the tibial bearing surfaces, at different amounts of flexion, is illustrated in FIG. 20, FIG. 21, and FIG. 22. As the knee bends toward a flexion of about 90°, the contact regions between the femoral condyles of femoral component 400 and their respective load bearing surfaces on tibial component 300 change. The orientation of the two components is illustrated in FIG. 20, which shows a partial cross-sectional view of the components at about 0° flexion. At this point in the knee movement, the medial femoral condyle 402 is retained at an effectively constant contact point upon its respective bearing surface of medial component 300. As further flexion occurs, illustrated in FIG. 21, medial femoral condyle 402 and lateral femoral condyle 401 translate posteriorly at different rates, causing rotational movement of the femoral component 400 upon the tibial component 300. FIG. 22 shows the partial cross-section of the two components after further knee flexion. Note that the contact points between femoral condyles 402 and 401 and their respective tibial bearing surfaces continue to translate posteriorly as flexion increases. This is due to the architecture of this embodiment, which is designed as a part of the knee movement based on the anatomical requirements of the natural knee joint. By way of further illustration, FIGS. 23-25 show a top-down partial cross-sectional view of the prosthesis during flexion of 45°, 90°, and 145°, respectively. FIGS. 24 and 25 illustrate this rotation during knee flexion from about 90° to about 145°. Tibial component 300 includes a higher projection on the medial anterior bearing surface, creating a medial anterior lip 303. FIG. 24 illustrates the knee prosthesis at about 90° flexion, where the femoral component has rotation R1 upon the tibial component. FIG. 25 illustrates the knee prosthesis at about 145° flexion, where the femoral component has rotation R2 upon the tibial component. Medial condyle 402 and lateral condyle 401 interact tibial component 300 at contact points. Although these further illustrations show knee flexion at 0°, 90°, and 145°, the range of motion allowed for in the embodiments of the present invention would be at least −10° (hyperextension) to about 165° (high flexion), with supported articulation in the medial and lateral compartments of the knee.

As can be seen from these views, this embodiment of the invention causes rotational movement, posterior translation, and other kinematic motion without a femoral cam, a tibial post, or a post/cam contact surface. The architecture of the medial and lateral femoral condyles, as well as the medial and lateral tibial bearing surfaces, drive a very precise medial pivot and femoral rotation in the transverse plane. This novel functionality of this embodiment of the present invention is useful in knee replacement procedures, especially in cruciate-retaining procedures where such functionality has not been possible prior to the present design.

What is claimed is:

1. A knee prosthesis comprising:
    a femoral component having two C-shaped condyles, each condyle having first and second free ends with an opening defined therebetween, the opening being defined by side walls extending anteriorly from the first free ends of the condyles to the second free ends of the condyles, the side walls sloping anteriorly and downward from a first point where the side walls join the first free ends of the condyles to a second point where the side walls join the second free ends of the condyles, wherein the side walls are joined together by the condyles that in turn are connected by a cam extending between and joining the first free ends of the condyles, wherein the opening is bounded by the anteriorly sloping sidewalls and the cam, the femoral component further comprising a convexly-curved medial side and a convexly-curved lateral side opposite the medial side, the medial side and lateral side tapering inwardly toward one another as the medial side and lateral side extend toward the second free ends of the condyles, wherein the medial side is tapered inwardly at a first angle, and the lateral side is tapered inwardly at a second angle, the second angle being greater than the first angle; and
    a tibial component having two bearing surfaces, each bearing surface supporting a corresponding one of the condyles, and a post disposed between the bearing surfaces and extending away from the bearing surfaces and towards the femoral component, the tibial component comprising an anterior cut defining a first uniformly sloping incline that slopes posteriorly and upward toward a posterior end of the tibial component, and the post comprising an anterior edge defining a second uniformly sloping incline that slopes posteriorly and upward toward the posterior end of the tibial component, the first and second uniformly sloping inclines defining a clearance path for a patellar implant thereby eliminating patellar post conflict;
    the femoral component and tibial component engaging each other by constant contact with the second free ends of the condyles and the bearing surfaces, and by selective contact between the cam and post during at least a portion of flexion between the femoral and tibial components;
    wherein moving the femoral and tibial components in flexion moves a contact region defined between the cam and post inferiorly and medially, resulting in medial rotation between the tibial and femoral components.

2. The knee prosthesis of claim 1, wherein the cam has an asymmetrical cross-section between its lateral end and medial end.

3. The knee prosthesis of claim 1, wherein the cam has an asymmetrical cross-section between a lateral end region and a medial end region, and the lateral end region has a larger cross-sectional area as compared to its medial end region.

4. The knee prosthesis of claim 1, wherein
    the femoral component has a medial condyle and a lateral condyle, the medial and lateral condyles of the femoral component being asymmetrical relative to each other;
    the two bearing surfaces of the tibial component comprise a medial bearing surface and a lateral bearing surface, the medial and lateral bearing surfaces being asymmetrical, and wherein the medial bearing surface has a projection defining a medial lip which encompasses the medial bearing surface;
    wherein moving the femoral and tibial components in flexion causes contact regions between the condyles and bearing surfaces to translate posteriorly at different rates and results in rotation between the tibial and femoral components.

5. The knee prosthesis of claim 4, wherein the second free end of the medial condyle has a uniform radial region where the medial condyle engages the medial bearing surface during flexion.

6. The knee prosthesis of claim 4, wherein an outer surface of the medial condyle engages the medial bearing surface during flexion, the outer surface having a first radii region, a second radii region, and a third radii region, each radii region defining a pivot point about which the medial condyle pivots and having a radius that is different from the other radii regions.

7. The knee prosthesis of claim 6, wherein the first radii region engages the medial bearing surface during flexion from 0° to 90°; the second radii region engages the medial bearing surface during flexion from 90° to 120°; and the third radii region engages the medial bearing surface during flexion from 120° to 165°.

8. The knee prosthesis of claim 4, wherein the medial lip and medial condyle prevent roll forward.

9. The knee prosthesis of claim 4, wherein the lateral bearing surface has a projection defining a lateral lip.

10. The knee prosthesis of claim 9, wherein the medial lip has a thickness $T_A$ and the lateral lip has a dimension $D_A$.

11. The knee prosthesis of claim 10, wherein a proportion of medial lip thickness $T_A$ and lateral lip dimension $D_A$ is 7:4.

12. The knee prosthesis of claim 9, wherein the lateral lip encompasses the lateral bearing surface.

13. The knee prosthesis of claim 4, wherein the femoral and tibial components engage in flexion from 0° to 165°.

14. The knee prosthesis of claim 1, wherein
    the medial condyle has a uniform radial region along the second free end, comprised of at least one radii, to engage the medial bearing surface during flexion; and
    wherein moving the femoral and tibial components in flexion from 0° to 90° causes the medial condyle to be retained by the medial anterior lip and prevents roll forward of the femoral component; and
    wherein moving the femoral and tibial components in flexion causes contact regions between the condyles and bearing surfaces to translate posteriorly at different rates and rotation between the tibial and femoral components.

15. The knee prosthesis of claim 14, wherein the medial condyle is retained by the medial lip when the femoral component engages the tibial component in flexion from 0° to 90°.

16. The knee prosthesis of claim 14, wherein the femoral and tibial components engage in flexion from 0° to 165°.

17. The knee prosthesis of claim 1, wherein engagement of the femoral and tibial components in flexion from 45° to 165° defines a contact region between the cam and post.

18. A knee prosthesis comprising:
    a femoral component having two C-shaped condyles, each condyle having first and second free ends with an opening defined therebetween, the opening is defined by side walls extending anteriorly from the first free ends of the condyles to the second free ends of the condyles, the side walls sloping anteriorly and downward from a first point where the side walls join the first free ends of the condyles to a second point where the side walls join the second free ends of the condyles, wherein the side walls are joined together by a cam extending between and joining the first free ends of the condyles, wherein the opening is bounded by the anteriorly sloping sidewalls and the cam, the cam having a larger cross-sectional area in its lateral region relative to its medial region, the femoral component further comprising a convexly-curved medial side and a convexly-curved lateral side opposite the medial side, the medial side and lateral side tapering inwardly toward one another as the medial side and lateral side extend toward the second free ends of the condyles, wherein the medial side is tapered inwardly at a first angle, and the lateral side is tapered inwardly at a second angle, the second angle being greater than the first angle; and a tibial component having two bearing surfaces, each bearing surface supporting a corresponding one of the condyles, and a post disposed between the bearing surfaces and extending away from the bearing surfaces and towards the femoral component, the tibial component comprising an anterior cut defining a first uniformly sloping incline that slopes posteriorly and upward toward a posterior end of the tibial component, and the post comprising an anterior edge defining a second uniformly sloping incline that slopes posteriorly and upward toward the posterior end of the tibial component, the first and second uniformly sloping inclines defining a clearance path for a patellar implant thereby eliminating patellar post conflict;

the femoral component and tibial component engaging each other by constant contact with the second free ends of the condyles and the bearing surfaces, and by selective contact between the cam and post during at least a portion of flexion between the femoral and tibial components;

wherein moving the femoral and tibial components in flexion moves the lateral region of the cam away from the post such that there is no contact between the cam and post at the lateral region of the cam at flexion of 145°.

19. The knee prosthesis of claim 18, wherein engagement of the femoral and tibial components in flexion from 45° to 165° moves the lateral region of the cam away from the post.

20. A knee prosthesis comprising:

a femoral component having two C-shaped condyles, each condyle having first and second free ends with an opening defined therebetween, the opening being defined by side walls extending anteriorly from the first free ends of the condyles to the second free ends of the condyles, wherein the side walls are joined together by the condyles that in turn are connected by a cam extending between and joining the first free ends of the condyles, wherein the opening is bounded by the sidewalls and the cam, the condyles comprising a medial femoral condyle and a lateral femoral condyle, the medial femoral condyle comprising a distal end having a first region that is defined by a first uniform radius of curvature $\alpha$, and a second region adjacent the first region that is defined by a second uniform radius of curvature $\beta$, the second uniform radius of curvature $\beta$ being different than the first uniform radius of curvature $\alpha$, the lateral femoral condyle comprising a distal end having a non-uniform radius of curvature, such that the medial femoral condyle and lateral femoral condyle are asymmetrical with respect to one another, the femoral component further comprising a convexly-curved medial side and a convexly-curved lateral side opposite the medial side, the medial side and lateral side tapering inwardly toward one another as the medial side and lateral side extend toward the second free ends of the condyles, wherein the medial side is tapered inwardly at a first angle, and the lateral side is tapered inwardly at a second angle, the second angle being greater than the first angle; and a tibial component having two bearing surfaces, each bearing surface supporting a corresponding one of the condyles, and a post disposed between the bearing surfaces and extending away from the bearing surfaces and towards the femoral component, the femoral component and tibial component engaging each other by constant contact with the second free ends of the condyles and the bearing surfaces, and by selective contact between the cam and post during at least a portion of flexion between the femoral and tibial components;

wherein moving the femoral and tibial components in flexion moves a contact region defined between the cam and post inferiorly and medially, resulting in medial rotation between the tibial and femoral components.

* * * * *